(12) United States Patent
Ma et al.

(10) Patent No.: US 8,268,344 B2
(45) Date of Patent: *Sep. 18, 2012

(54) PARTICLE-CONTAINING COMPLEX POROUS MATERIALS

(75) Inventors: Peter X. Ma, Ann Arbor, MI (US); Guobao Wei, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1308 days.

This patent is subject to a terminal disclaimer.

(21) Appl. No.: 11/410,480

(22) Filed: Apr. 25, 2006

(65) Prior Publication Data

US 2006/0246121 A1    Nov. 2, 2006

Related U.S. Application Data

(60) Provisional application No. 60/675,247, filed on Apr. 27, 2005.

(51) Int. Cl.
*A61K 9/70* (2006.01)
(52) U.S. Cl. ........................................................ 424/443
(58) Field of Classification Search .................... 424/443
See application file for complete search history.

(56) References Cited

U.S. PATENT DOCUMENTS

| | | | | |
|---|---|---|---|---|
| 4,818,542 A | * | 4/1989 | DeLuca et al. | 424/491 |
| 5,318,779 A | * | 6/1994 | Hakamatsuka et al. | 424/426 |
| 6,582,471 B1 | * | 6/2003 | Bittmann et al. | 623/23.63 |
| 6,673,285 B2 | * | 1/2004 | Ma | 264/49 |
| 6,790,455 B2 | * | 9/2004 | Chu et al. | 424/423 |
| 2002/0122828 A1 | * | 9/2002 | Liu | 424/497 |
| 2003/0219466 A1 | * | 11/2003 | Kumta et al. | 424/423 |
| 2006/0019264 A1 | | 1/2006 | Attiya et al. | |

FOREIGN PATENT DOCUMENTS

WO    WO 03/033580    *    4/2003

OTHER PUBLICATIONS

International Search Report for S.N. PCT/US2006/015612 dated Dec. 5, 2006 (7 pages).

* cited by examiner

*Primary Examiner* — Brandon Fetterolf
*Assistant Examiner* — Shirley V Gembeh
(74) *Attorney, Agent, or Firm* — Dierker & Associates, P.C.

(57) ABSTRACT

Porous materials and methods for forming them are disclosed. One method for immobilizing micro-particles and/or nano-particles onto internal pore surfaces and/or external pore surfaces of porous materials includes suspending the micro-particles and/or nano-particles in a liquid adapted to swell, soften, and/or deform either the porous materials and/or the particles, thereby forming a liquid-particle suspension. The method further includes adding the suspension to the porous materials; and removing the liquid, thereby forming the porous materials having the micro-particles and/or nano-particles immobilized on the internal pore surfaces and/or the external pore surfaces.

4 Claims, 14 Drawing Sheets

FIG. 3C
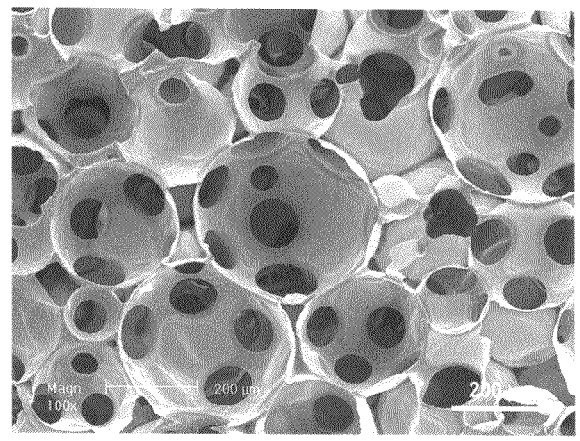
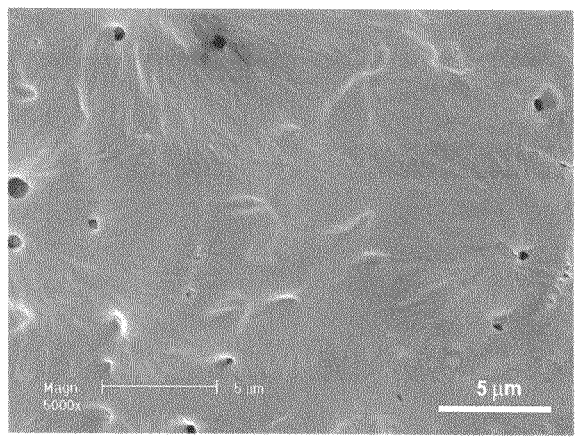
FIG. 3D
FIG. 4A
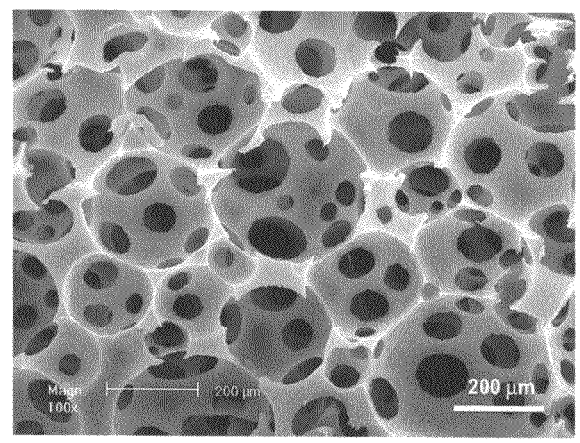

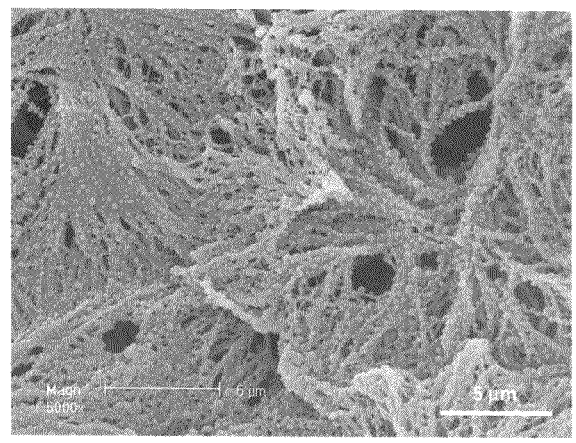
FIG. 4B
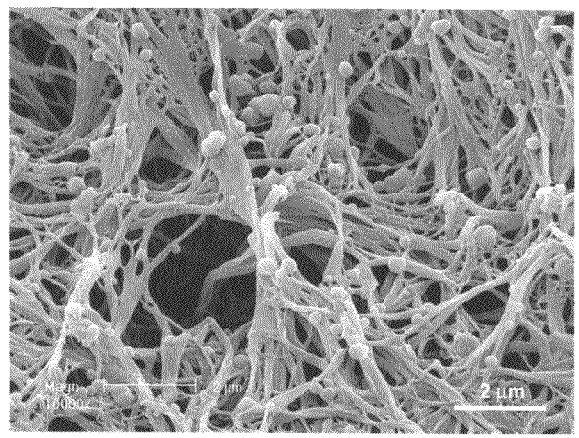
FIG. 4C
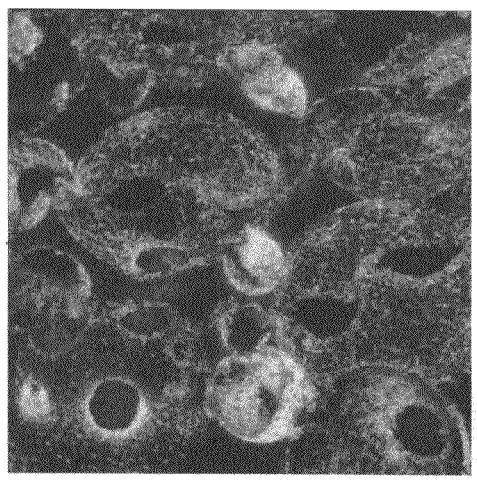 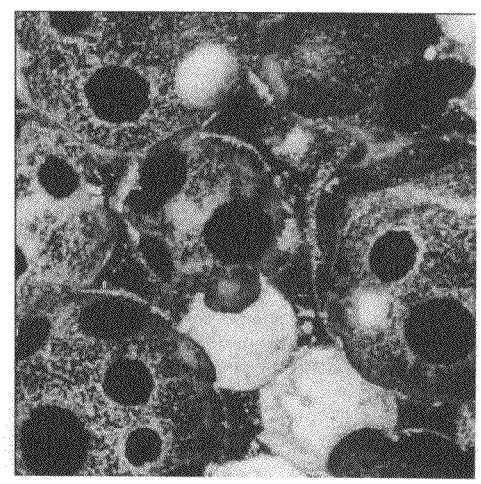
FIG. 4D　　　　FIG. 4E

FIG. 5D
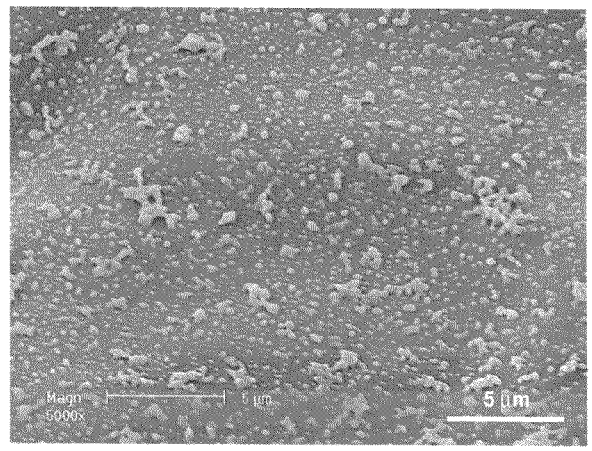
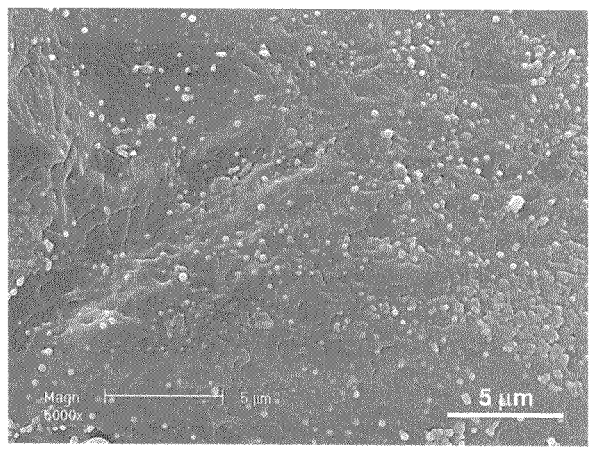
FIG. 5E
FIG. 6A
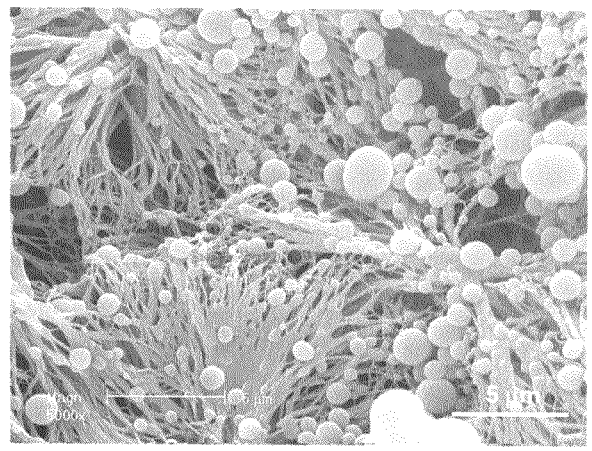

FIG. 6B
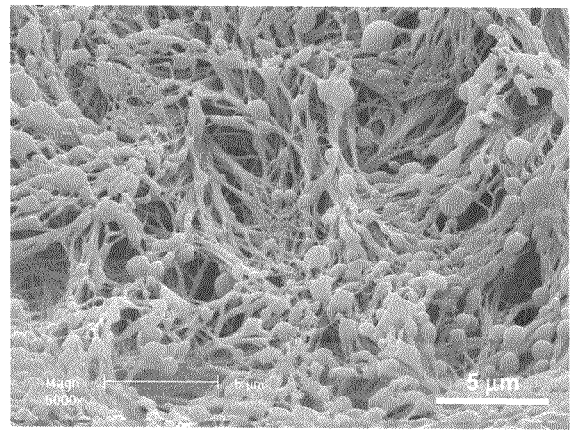
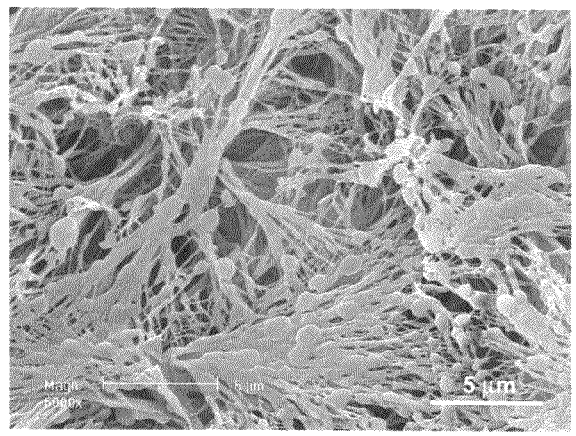
FIG. 6C
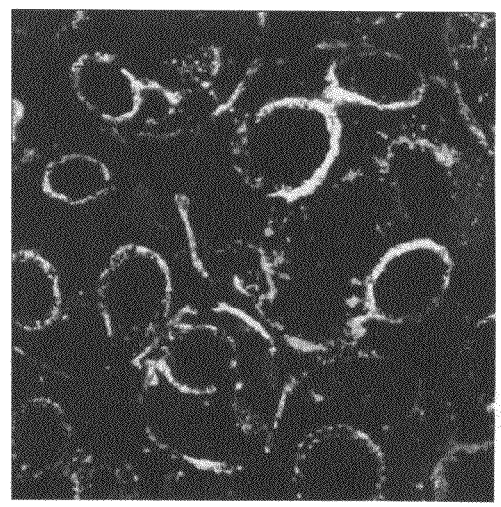
FIG. 7A

PLGA50-6.5K
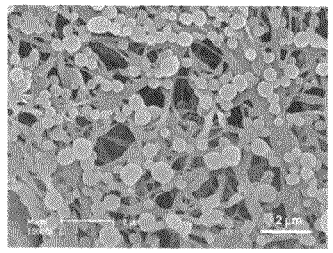
0 Days
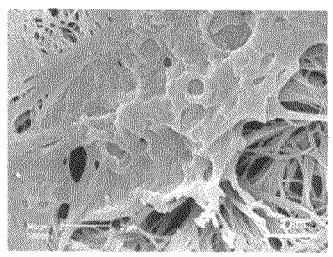
3 Days
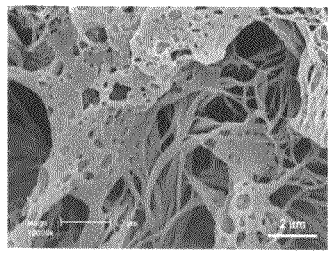
7 Days
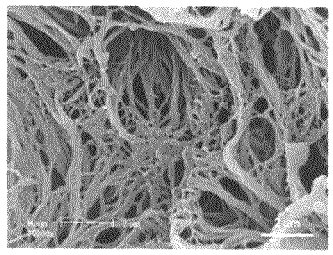
21 Days
PLGA50-64K
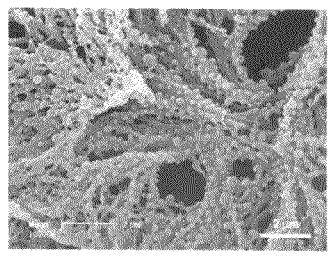
0 Days
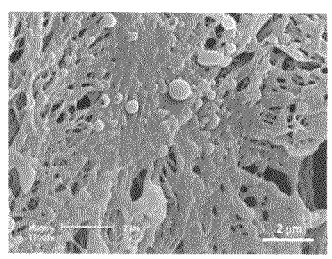
10 Days
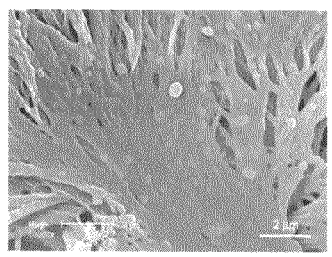
21 Days
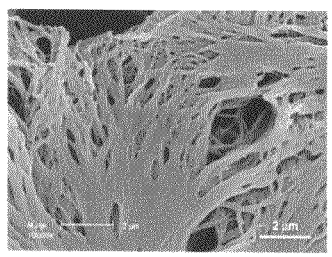
35 Days
FIG. 12A
FIG. 12B

PLGA75-113K

0 Days

21 Days

35 Days

56 Days

PARTICLE-CONTAINING COMPLEX POROUS MATERIALS

CROSS REFERENCE TO RELATED APPLICATIONS

This application claims the benefit of U.S. Provisional Patent application Ser. No. 60/675,247 filed on Apr. 27, 2005.

STATEMENT REGARDING FEDERALLY SPONSORED RESEARCH OR DEVELOPMENT

This invention was made in the course of research supported by a grant from the National Institutes of Health (NIH) and the National Institute of Dental and Craniofacial Research (NIDCR), Grant Nos. DEO15384 and DEO14755. The U.S. government has certain rights in the invention.

BACKGROUND

The present disclosure relates generally to controlled release therapeutic materials, and more particularly to such materials formed from particle-containing complex porous materials.

Controlled release of biologically active agents using polymeric materials is a powerful means for a wide variety of therapeutics. Such approaches may be especially advantageous for delivery of therapeutic agents to a localized area to substantially circumvent unwanted systemic side effects, to achieve high local dosages without the use of large quantities of therapeutic agents, and/or to prevent unnecessary destruction or denaturing of the agents in the delivery routes (such as in circulation or the gastrointestinal track).

Though different from drug delivery, tissue engineering/regenerative medicine is another interdisciplinary and multi-disciplinary field, which aims to generate biological replacements for damaged tissues, failing organs, and dysfunctional body parts. Still young and growing, the field significantly challenges the current treatment modalities represented by transplantation, surgical reconstruction, and the usage of prostheses, each of which has inherent limitations. In tissue engineering/regenerative medicine, an artificial temporary extracellular matrix (a.k.a. scaffold) plays an important role as a 3D guidance for cell adhesion, proliferation, and new tissue organization. These scaffold materials are compatible with cells and biological host environments. Such scaffolds also possess the appropriate porous structure suitable for cell penetration, nutrient supplies, and metabolic waste removal. Desirably, they may also encourage needed cell-cell and cell-matrix interactions; and may be biodegradable to eventually fade away after fulfilling the purpose as templates (as this may obviate long-term foreign body reactions and associated complications).

In addition to cells and scaffolds, biological signaling may also be necessary for cell function and tissue regeneration. Endogenous signaling molecules are often not sufficient in quantities or types for regeneration purposes, where the addition of signaling molecules is desirable. For example, when stem cells are used for regeneration, the lineage control often relies on the use of differentiation factors. For in vitro cultures, addition of biological molecules in a culture medium either in a continuous or discrete fashion is often possible. In an in vivo situation, such addition of factors to a cell-scaffold construct or regenerating tissue may be very challenging, if not virtually impossible. Due to the sensitivity of cells to the concentration of biological molecules and because of the short half-lives of many of these agents, controlled release technologies are being introduced into the field of tissue engineering and regenerative medicine.

Many controlled release techniques may potentially be introduced into tissue engineering scaffolds. Those that are relatively easy to adapt have been recently utilized for tissue engineering applications. For example, hydrogels have been used as both drug delivery matrices and tissue engineering scaffolds. Further, growth factors, along with cells, have been incorporated into hydrogel scaffolds to enhance regeneration.

Similarly, biological agents have also been directly added into a polymer or a blend of polymers, and the mixture is then used to fabricate a scaffold. For example, ascorbate-2-phosphate and dexamethasone (AsAP and Dex, agents to enhance osteoblastic differentiation of cells) have been mixed in chloroform, which was used to dissolve poly(d,1-lactide-co-glycolide) (PLGA). This resulted in a mixture (Dex and AsAP suspended in a PLGA solution). This polymer suspension was mixed with salt particles to fabricate a scaffold using the salt-leaching technique, i.e., after the evaporation of solvent, the salt particles were leached away by water to form pores. Others used a PLLA-PDGF (platelet derived growth factor) emulsion to fabricate foams via freeze-drying, polymers mixed with plasmid DNA to fabricate meshes via electrospinning, or a PLGA-bFGF (basic fibroblast growth factor) emulsion to fabricate porous materials using supercritical $CO_2$ foaming.

There also have been attempts to modify a scaffold with biologically active agents using certain coating techniques. For example, collagen matrix was partially dipped in growth factor solutions, such as bFGF, HGF (hepatocyte growth factor), PDGF-BB, VEGF (vascular endothelial growth factor), or IGF-1 (insulin like growth factor-1), to coat these factors on the matrix. Porous bioglass materials have been coated with a laminin solution to allow for subsequent slow release. An emulsion of a polymer solution and vitamin $B_{12}$ solution has been used to coat certain porous polymer materials. Basic fibroblast growth factor (bFGF) was complexed with sucralfate and polyHEMA and then coated on PLLA scaffolds to enhance liver tissue formation.

The above-described methods of bioactive agent incorporation may, in some instances, achieve certain slow release purposes, but the control over release profile of a bioactive agent is generally limited. Further, these methods are not suitable for releasing multiple agents with individualized controlled release profiles.

Attempts have been made to use micro- and/or nanospheres or particles (also referred to herein as "MNS" and/or "MNP", these abbreviations meaning herein, micro-spheres/-particles, nano-spheres/-particles, or combinations thereof) made of polymers (often biodegradable polymers) for incorporating drugs and proteins for controlled release. Attempts are also being made to incorporate the controlled release capacity into scaffolding materials to provide desired bioactive agents. However, the successful realization of such ideas to date has proven technically challenging.

One way of combining factor-containing MNS/MNP with scaffolding materials is to directly load MNS/MNP into a scaffold. For example, MNS/MNP containing transforming growth factors (TGF-$\beta_1$) have been added into a scaffold to aid chondrogenesis. Gelatin MNS/MNP containing bFGF have been mixed with preadipocytes and dripped on collagen sponge sheets to engineer adipose tissue. However, this method is limited because the added MNS/MSP may migrate under gravity, physical motion, mechanical interference (stirring, shaking, mechanical stress and so forth), and/or fluid flow. Such migrations may deleteriously lead to undesired distribution or loss of MNS/MNP.

PLGA MNS/MNP encapsulating IGF-I (insulin-like growth factor) and TGF-$\beta_1$ have been entrapped together with condrocytes in a photopolymerized PEO (polyethylene oxide) hydrogel for cartilage formation. Advantages of such in situ gelling systems include the ability to fill irregularly shaped tissue defects, allowing minimally invasive procedures (such as injection and arthroscopic surgery), and the ease of cell and MNS/MNP incorporation. However, the disadvantages include the non-degradability of PEO, the lack of control over macro- and micro-pore shape and size in the gels, and poor mechanical properties.

Similarly, bFGF-containing PLGA MNS/MNP have been incorporated into alginate gel and crosslinked. The alginate gel was then lyophilized to form solid porous materials as a membrane to release bFGF for enhanced angiogenesis and wound healing. The advantage of this method is that the solid-state form may be more mechanically stable than gels. The disadvantages include the lack of matrix degradability (alginate), the inability of controlling pore shape, and the limited ability of varying pore size. Although different from hydrogels, calcium-phosphate cement was also loaded with PLGA MNS/MNP to release rhBMP-2 (recombinant human bone morphogenetic protein-2). Unfortunately, this system generally has similar disadvantages such as the lack of degradability, and the inability of controlling pore shape and pore size.

Another method of entrapping PLGA MNS/MNP into a porous scaffold is gas foaming. In gas foaming, carbon dioxide ($CO_2$) is usually used as a foaming agent. Solid polymer disks are exposed to high pressure $CO_2$ to allow saturation of $CO_2$ in the polymer. Thermodynamic instability is then created by rapidly releasing $CO_2$ gas from the polymer system, followed by the nucleation and growth of gas bubbles in the material. This method allows protein or DNA powders or PLGA MNS/MNP to be entrapped in the materials. However, the disadvantages of this method include the lack of control over pore size and shape, and a nonporous surface, closed-pore structure, with only between about 10% and about 30% of interconnected pores. The porosity and interpore connectivity may, in some instances, be improved by combining salt-leaching techniques with the gas foaming process, although eliminating closed pores has yet to be successfully achieved. Additionally, the leaching process may remove a large portion of the incorporated agents in an uncontrolled manner, which is also not desirable. Furthermore, the embedded MNS/MNP in the walls of the porous materials generally lose the desired release profiles of the MNS/MNP.

To make it feasible to suspend PLGA micro-/nano-spheres or particles in a PLGA solution, PLGA MNS/MNP have been coated with a layer of PVA (polyvinyl alcohol). The PLGA solution with suspended PVA-coated MNS/MNP was used with salt particles to fabricate scaffolds based on salt-leaching techniques. Theoretically, the PVA coating does not dissolve in organic solvents such as THF (tetrahydrofuran), thereby potentially preventing the dissolution of PLGA MNS/MNP in a PLGA solution. However, a defect-free PVA layer on a MNS/MNP in suspension has yet to be easily, reproducibly and successfully achieved. Additionally, the embedded MNS/MNP inside the pore walls may not result in controlled release profiles.

As such, it would be desirable to provide controlled release therapeutic materials having desirable control over release profiles of bioactive agent(s). Further, it would be desirable to provide such materials suitable for releasing multiple agents. Still further, it would be desirable to provide such materials with individualized controlled release profiles.

SUMMARY

Porous materials and methods for forming the same are disclosed. One of several methods disclosed herein for immobilizing at least one of micro-particles and nano-particles onto internal pore surfaces and/or external pore surfaces of porous materials includes suspending the micro-particles and/or nano-particles in a liquid adapted to swell, soften, and/or deform either the porous materials and/or the particles, thereby forming a liquid-particle suspension. The method further includes adding the suspension to the porous materials; and removing the liquid, thereby forming the porous materials having the micro-particles and/or nano-particles immobilized on the internal pore surfaces and/or the external pore surfaces.

BRIEF DESCRIPTION OF THE DRAWINGS

Objects, features and advantages of embodiments of the present disclosure will become apparent by reference to the following detailed description and drawings, in which:

FIGS. 3C and 3D are each SEMs of PLLA microporous/solid scaffolds, showing a PLLA macroporous scaffold with solid pore wall structures;

FIGS. 4A and 4B are each SEMs of PLLA nano-fibrous scaffolds post seeded with PLGA microspheres, showing well maintained macroporous and nano-fibrous scaffolds incorporated with about 1.6 mg PLGA50-64K MS;

FIG. 4C is a SEM of PLLA nano-fibrous scaffolds post seeded with PLGA microspheres, showing well maintained macroporous and nano-fibrous scaffolds incorporated with about 0.16 mg PLGA50-64K MS;

FIG. 4D is a Laser scanning confocal micrograph at 200× of a microsphere-incorporated nano-fibrous PLLA scaffold, post-seeded with TRITC-BSA/PLGA50-6.5K (red) and FITC-BSA/PLGA50-64K (green) microspheres;

FIG. 4E is a Laser scanning confocal micrograph at 200× of a microsphere-incorporated nano-fibrous PLLA scaffold post-seeded with PLGA50-64K microspheres encapsulating TRITC-BSA (red) and FITC-dextran (green);

FIGS. 5C and 5D are each SEMs of microsphere-incorporated solid-walled PLLA scaffold;

FIG. 5E is a SEM of microsphere-incorporated in a solid-walled PLGA85 scaffold;

FIG. 6A is a SEM of a PLGA50-64K microsphere-incorporated PLLA nano-fibrous scaffold without solvent/non-solvent treatment;

FIG. 6B is a SEM of a PLGA50-64K microsphere-incorporated PLLA nano-fibrous scaffold treated with 80 μl hexane/THF (90/10, v/v);

FIG. 6C is a SEM of a PLGA50-64K microsphere-incorporated PLLA nano-fibrous scaffold treated with ethanol/acetone (90/10, v/v);

FIG. 7A is a Laser scanning confocal micrograph at 200× of PLLA nano-fibrous scaffolds pre-seeded with TRITC-BSA/PLGA50-6.5K (red) and FITC-BSA/PLGA50-64K (green) microspheres;

FIG. 12A is a degradation characterization of PLGA microspheres after post-seeded into PLLA nano-fibrous scaffold using scanning electron microscopy at 10,000×, PLGA50-6.5K at 0, 3, 7, 21 days;

FIG. 12B is a degradation characterization of PLGA microspheres after post-seeded into PLLA nano-fibrous scaffold using scanning electron microscopy at 10,000× PLGA50-64K at 0, 10, 21, 35 days;

DETAILED DESCRIPTION OF THE EMBODIMENTS

Figure 1A:
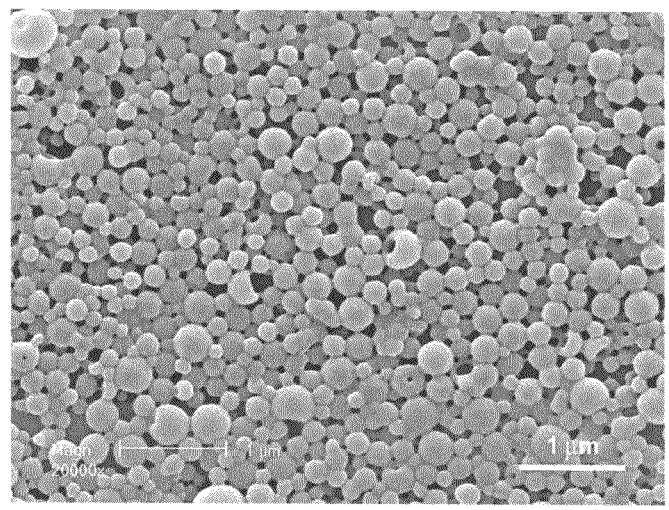
FIG. 1A is a scanning electron micrograph (SEM) of PLGA50-64K microspheres.

The present inventors have unexpectedly and fortuitously discovered compositions incorporating micro-particles/spheres (ranging from about $10^{-6}$ m to about $10^{-3}$ m in dimension) or nano-particles/spheres (ranging from about $10^{-9}$ m to about $10^{-6}$ m in dimension) that may contain a single agent or multiple agents (molecules, ions, and/or their complexes) individually or in combination into a variety of porous materials; as well as methods for forming the same. Such complex porous materials allow for the release of various agents in a controlled fashion. The present methods and/or compositions substantially, advantageously overcome various limitations of the technologies described hereinabove.

In the embodiments disclosed herein, the materials of the particles and/or porous foam material(s) may be any natural or synthetic materials; organic materials, inorganic materials, metallic materials, composites thereof, and/or combinations thereof. In an embodiment, the materials are organic materials. They may be natural or synthetic macromolecules. In one embodiment, the materials are at least one of polymers, proteins, carbohydrates, lipids, and combinations thereof.

Some suitable non-degradable polymers include, but are not limited to water insoluble (hydrophobic) polymers/macromolecules that are suitable include polytetrafluoroethylene (PTFE), polyvinylchloride (PVC), polyethylenes (PE), polypropylenes (PP), polystyrenes, polyacrylonitrile (PAN), polymethylmethacrylate (PMMA), polyvinylacetate (PVAc), polyphenylene oxide, polypropylene oxide (PPO), polyvinylidene fluoride (PVDF), polybutylene, polyamides (PA, Nylons), polyesters, polycarbonates, polyurethanes, polysiloxanes, polyimides, polyetheretherketone (PEEK), polysulfones, polyethersulphone, cellulose, polysaccharides and their derivatives, and mixtures thereof. When in situ polymerization is used instead of polymers/macromolecules, some exemplary suitable hydrophobic unsaturated monomers include the following: acrylates, methacrylates (eg. methyl methacrylate), ethylene, propylene, tetra-fluoroethylene, styrene, vinyl chloride, vinylidene chloride, vinyl acetate, acrylonitrile, 2,2-bis[4-(2-hydroxy-3-methacryloyloxy-propyloxy)-phenyl]propane (Bis-GMA), ethyleneglycol dimethacrylate (EGDMA), tri-ethyleneglycol dimethacrylate (TEGDMA), bis(2-methacryly-oxyethyl) ester of isophthalic acid (MEI), bis(2-meth-acrylyoxyethyl) ester of terephthalic acid (MET), bis(2-methacrylyoxyethyl) ester of phthalic acid (MEP), 2,2-bis(4-methacrylyoxy phenyl) propane (BisMA), 2,2-bis[4-(2-methacrylyloxyethoxy) phenyl]propane (BisEMA), 2,2-bis[4-(3-methacrylyloxy-propoxy) phenyl] propane (BisPMA), hexafluoro-1,5-pentanediol dimethacrylate (HFPDMA), bis-(2-methacrylyloxyethoxy-hexafluoro-2-propyl) benzene [Bis(MEHFP)φ], 1,6-bis(methacrylyloxy-2-ethoxycarbonylamino)-2,4,4-tri-methylhexan (UEDMA), spiro orthocarbonates, other vinyl monomers, the derivatives of these monomers, and mixtures thereof. Monomers of condensation polymers may also be used to form the porous materials in situ. Some exemplary monomer types in this category are diacids and diols (pairs), co-hydroxy carboxylic acids, lactones, diacids and diamines (pairs), amino acids, lactams, diisocyanates, diols (pairs), and/or combinations thereof.

Biodegradable polymers and macromolecules may also be used, especially when controlled release properties are desired. Some exemplary, non-limitative biodegradable polymers are given here: poly(lactide-co-glycolide) (PLGA), poly (L-lactic acid) (PLLA), poly(D,L-lactic acid) (PDLLA), polyglycolic acid (PGA), polyanhydrides, poly(ortho ethers), poly(ε-caprolactone) (PCL), poly(hydroxy butyrate) (PHB), poly(propylene fumarate) (PPF), polyphosphoesters (PPE), polyphosphazenes, and/or mixtures thereof. There are also degradable natural macromolecules (typically enzymatically degradable) such as collagen, gelatin and many other proteins, carbohydrates, and/or their derivatives. Some exemplary, non-limitative water-soluble (hydrophilic) polymers/macromolecules that are suitable materials include polyvinyl alcohol, polyethylene oxide (polyethylene glycol), polymethacrylic acid (PMAA), polyvinyl pyrolidone, polyacrylic acid, poly(lysine), poly(allylamine), poly(ethylenimine), poly(acrylamide), poly(acrylamide-co-arylic acid), poly (acrylamide-co-diallyldimethylammonium chloride), poly (vinyl alcohol), poly(ethylene glycol), polyethylene-block-poly(ethylene glycol), poly(propylene glycol), poly(2-hydroxypropyl methacrylate), poly(2-hydroxyethyl methyacrylate), poly(4-hydroxystrene), polyethylene monoalcohol, poly(vinyl alcohol-co-ethylene), poly(styrene-co-allyl alcohol), hydroxyethylcellulose, alginate, pectin, chitin, chitosan, dextran, hyaluronic acid, collagen, gelatin, and/or mixtures thereof.

Certain such polymers/macromolecules can also be synthesized in situ for the porous materials fabrication. Some exemplary suitable acid-containing hydrophilic monomers include the following: monomers containing carboxylic acid: acrylic acid, methacrylic acid, 4-vinylbenzoic acid, crotonic acid, oleic acid, elaidic acid, itaconic acid, maleic acid, fumaric acid, acetylenedicarboxylic acid, tricarbollylic acid, sorbic acid, linoleic acid, linolenic acid, eicosapentaenoic acid, other unsaturated carboxylic acids, anhydrides, their derivatives, and mixtures thereof; other organic acids such as sulfonic acid, and/or phosphonic acid replacement of the carboxyl group of the above listed unsaturated carboxylic acids, their derivatives, and mixtures thereof. Some exemplary suitable amine-containing hydrophilic monomers include allylmine, 4-vinylaniline, L-lysine, D-lysine, DL-lysine, acrylamide, their derivatives, and mixtures thereof. Some exemplary suitable hydroxyl-containing hydrophilic monomers include 2-hydroxypropyl methacrylate, 2-hydroxyethyl methacrylate, 4-hydroxystrene, ethylene glycol, propylene glycol, poly(ethylene glycol) acrylate, poly(ethylene glycol) methacrylate, their derivatives, and/or mixtures thereof.

Many natural macromolecules and synthetic polymers may be both hydrophilic and hydrophobic (amphiphilic). They could also be used for certain foam or particle preparations, such as those containing acid, amine, hydroxyl, and/or other hydrophilic groups in some or all of their structural units. Many of them are copolymers in some way containing both hydrophilic and hydrophobic moieties.

The agents incorporated in the controlled release particles (i.e., the micro-particles and/or nano-particles (MNS/MNP)) can be proteins, hormones, DNA, RNA, nutrients, drugs, other biologically regulating agents, and/or the like. It is to be understood that the agents (molecules, ions, or mixtures thereof) are not limited to applications to stimulate cell adhesion, growth, and tissue regeneration. They may be any drugs, pain suppressors, anti-inflammatory agents, sterilizing agents, contraceptives, pesticides, fertilizers, fragrances, spices and so forth. Furthermore, the agents do not have to be biologically active. They could be functional in other ways, such as, for example, controlling pH, varying colors, imparting fluorescence, maintaining humidity, adjusting conductivities, or as morphological modifications.

Some exemplary, non-limitative biologically active agents include bone morphogenetic proteins (such as BMP-2, BMP-3, BMP-4, BMP-6, BMP-7 and so forth), transforming growth factors (TGFs, such as TGF-α and TGF-β), acid fibroblast growth factor (aFGF) and basic fibroblast growth factor (bFGF), platelet-derived growth factor (PDGF, PDGF-BB and so forth), epidermal growth factor (EGF), vascular endothelial growth factor (VEGF), hepatocyte growth factor (HGF), nerve growth factor (NGF), insulin, insulin-like growth factors (IGFs), parathyroid hormone (PTH), parathyroid hormone related protein (PTHrP), DNAs that encode various factors including the above listed, double-stranded RNAs (dsRNAs) that interfere (silence) the genes of various factors including the above listed, various biologically functional peptides (RGD and so forth), vitamins, ascorbate-2-phosphate, dexamethasone, 1-glutamine, and so forth. These agents may be delivered alone or in combination to achieve individualized or synchronized delivery to achieve synergistic or additive effects, as partially demonstrated in some examples presented further in this disclosure.

It is to be understood that an already fabricated porous material may be used. In these embodiments, the methods generally include immobilizing the micro-/nano-spheres/particles onto the surfaces of internal and external pores of the pre-fabricated porous material. In this specific technology, the micro-/nano-spheres/particles (with or without agents to be released) are suspended in a non-solvent of both the particles and the porous material. The suspension is then added into the porous material.

After evaporation of the non-solvent, the particles are loosely adhered on the internal and external pore surfaces of the porous material. By "loosely adhered," it is meant that the particles could be washed away using a non-solvent of the particles.

Then, a liquid that swells, deforms, or slightly dissolves either or both of particles and porous material (such as a relatively poor solvent, or a mixture of a solvent and a non-solvent of the particles and/or the porous material) is added into the porous materials with the loosely adhered particles. As used herein, the swelling/deforming/slightly dissolving/softening (mentioned below) is meant to mean changes that do not substantially affect the release profiles of the particles and/or porous materials. Significantly swelling, deforming, and/or dissolving would generally affect the release profiles of the incorporated agents.) The liquid helps the particles to strongly adhere to the internal and external pore surfaces. After the treatment, the liquid is removed (via freeze-drying, vacuum drying, evaporation, or exchange with a non-solvent for neither the particles nor the porous material). This will result in a porous material with strongly adhered micro-/nano-particles on the pore surfaces. By "strongly adhered" is meant that the particles are not easily washed away using a non-solvent of the particles.

In another embodiment, the porous material is fabricated as the immobilization of the MNS/MNP takes place. It is to be understood that (as mentioned herein), template materials (also called porogens) may be used in the fabrication and immobilization processes.

A material can be made into a template, or small geometrical (regular or non-regular) elements can be assembled or aggregated into a 3D template. The template is the negative replica of the porous material to be fabricated. The 3D template can be made using various technologies such as programmed fabrication automatically by a machine (rapid prototyping) or batch by batch manually or semi-manually. As a non-limiting example, the geometrical element(s) (one example of which is a sugar sphere) is/are formed via emulsification, solvent extraction, and freeze- or air-drying. It is to be understood that the template/porogen may be formed of any suitable material, non-limitative examples of which are selected from gelatins, collagen, proteins, polypeptides, carbohydrates, polysaccharides, alginate, chitin, chitosan, pectin, salts, sodium hydroxide, sugars, waxes, naphthalene, natural or synthetic water soluble polymers, natural or synthetic non-water soluble polymers, degradable polymers, non-degradable polymers, partially degradable polymers, or combinations thereof.

Generally, in an embodiment in which the template/porogen material is a sugar sphere template/porogen is formed by first making individual sugar spheres, and then bonding the spheres together. To form individual spheres, a sugar material is melted to form a liquefied sugar material. It is to be understood that any suitable sugar material (e.g., carbohydrates that are aldehyde or ketone derivatives of polyhydric alcohols) may be used. Some non-limitative examples of suitable sugar materials include sucrose, maltose, dextrose and fructose. It is to be further understood that L-sugars, D-sugars, or combinations thereof may be used. In an embodiment, D-fructose is used. The temperature at which the sugar material is melted will depend upon the sugar material selected. For example, a D-fructose material melts at about 120° C., when exposed to the heat for about 90 minutes.

The liquefied sugar is then emulsified with a liquid that does not dissolve the sugar (i.e. a non-solvent to the sugar), one non-limitative example of which is mineral oil. In an embodiment, the emulsion is formed at a temperature of about 120° C. The emulsion is then cooled, for example, in an ice-bath. The cooling results in the solidification of emulsion and the formation of the sugar spheres. Any remaining emulsion mixture (e.g., the non-solvent to the sugar) is discarded, and the sugar spheres may be washed/rinsed in any suitable non-solvent to sugar. Some non-limitative examples of suitable non-solvent to sugar washing liquids include hexane, cyclohexane, and/or the like, and/or combinations thereof. The sugar spheres may then be sieved. Desirable sizes for the individual sugar spheres range from about 20 µm to about 2 mm. In an alternate embodiment, the sizes range from about 50 µm to 1 mm; and in a further alternate embodiment, from about 180 µm to about 600 µm.

To form a sugar sphere template, the individual sugar spheres may be packaged in a container/mold within a substantially non-hydrous environment and treated at a predetermined temperature for a predetermined time, sufficient for the spheres to bond. Without being bound to any theory, it is believed that better control of the sugar spheres is achieved in a substantially non-hydrous environment wherein the sugar spheres do not substantially absorb water from the environment. It is to be understood that any suitable non-hydrous environment may be used, some examples of which include, but are not limited to hexane, other non-hydrous organic liquids, dried air, a vacuum, inert gas(es) (e.g. nitrogen gas), or combinations thereof. It is to be understood that the predetermined temperature and predetermined time may be any as suitable or desired. In a non-limitative example, the predetermined time ranges from about 2 minutes to about 12 hours; and in an alternate embodiment, ranges from about 5 minutes to about 3 hours. In a further non-limitative example, the predetermined temperature ranges from about room temperature to about 100° C.; and in an alternate embodiment, ranges from about 35° C. to about 60° C. In a further alternate embodiment, the predetermined temperature is about 37° C. Once bonded, if the non-hydrous environment is a liquid in which the sugar spheres are contained (e.g. hexane), the liquid non-hydrous environment may be removed and the template dried under vacuum.

It is to be understood that the template/porogen may be formed from a predetermined three-dimensional configuration of the material(s) (non-limitative examples of which are described herein). The predetermined three-dimensional configuration of the template/porogen may have any desirable shape, size, surface morphology, and/or combinations thereof. It is to be understood that the configuration of the template/porogen may depend, at least in part, on the desired geometry and/or configuration of the porous material to be formed.

In an embodiment in which geometrical elements are assembled to form the template/porogen, non-limitative examples of the geometrical element shapes include cubic or other geometrically shaped crystals, spheres (e.g., sugar spheres discussed herein), fibers, discs, regular geometric shapes, irregular geometric shapes, and/or combinations thereof.

A suspension of the micro-/nano-particles (with or without agents to be released) in a liquid (may be a mixture) is added onto such a template to coat the complex 3D surface. The liquid is then removed.

Another liquid (such as a polymer solution, suspension, or non-polymer solution or suspension) is cast onto the coated template to form a system.

Any volatile components are removed from the system (such as a solvent, a non-solvent, or a mixture) to form a complex material that includes the template, the micro-/nano-spheres/particles, and the non-volatile components of system. Removal of the volatile component(s) may be accomplished in any suitable fashion, such as by evaporation, freeze-drying, sublimation, extraction, and/or the like, and/or combinations thereof. The template material is then removed via any suitable process (such as, for example, dissolving away in a solvent, melting, degrading, and/or the like, and/or combinations thereof). A complex 3D porous material is produced with the immobilized MNS/MNP on the interior surfaces.

In still other embodiments, MNS/MNP are suspended in liquids that can swell, soften, partially dissolve, and/or deform the particles and/or the porous material, but does not dissolve the MNS/MNP and material(s) used to make the porous (foam) material. The MNS/MNP may be suspended in either the liquid or the solution to form a suspension. The suspension is then cast into a mold or on the template of the porous material. In an embodiment in which the liquid suspension is used, the liquid may be removed, and the particles are left strongly adhered on the internal and external surfaces of the porous material. In an embodiment in which the solution suspension is used, the solvent of the liquid (such as a polymer solution or suspension) may be removed (e.g., via evaporation, vacuum drying, freeze drying, sublimation, or being extracted with a non-solvent of the material), and the MNS/MNP are left entrapped in or on the walls of the formed porous material. A non-limitative example of the composition formed from either of these embodiments includes immobilized alginate/chitosan microspheres in PLLA nano-fibrous scaffolds with or without macro-pores.

It is to be understood that multiple types of micro- and/or nano-particles (containing different agents to be released) are allowed to be entrapped in/on the internal and external pore walls of the porous materials using any single or different combinations of the embodiments disclosed herein. Such complex porous materials will allow the tailoring of individualized release profiles for a variety of different agents.

Furthermore, any of the embodiments described herein may be formed so that the walls of the porous materials are nano-fibrous (such as those formed using a phase separation technology described in at least some of the examples). The nano-fibrous matrix may also be formed via other techniques, such as electrospinning. It is believed that the nano-fibrous materials provide better 3D transport, such as, for example, better diffusion conditions for released agents. As such, the nano-fibrous porous materials may allow additional control over the release profiles of the agents contained in the micro-/nano-spheres/particles.

It is to be understood that the pore size of the porous materials described herein may be designed in the nano-size range ($10^{-9}$ to $10^{-6}$ m in dimension), micro-size range ($10^{-6}$ to $10^{-3}$ m in dimension), macro-size range ($10^{-3}$ m or larger in dimension), or multiple size ranges, although some preferred size ranges are the nano-size, micro-size, the lower end of the macro-size ($10^{-3}$ to $10^{-2}$ m), and/or combinations thereof.

It is to be further understood that the porosity of the porous materials may be 30% or higher, preferably 50% or higher. In an embodiment, the porosity ranges between about 75% and about 99%.

In any of the embodiments described herein, it is to be understood that the particle shapes may be regular or irregular, including but not limited to spherical, rod-like, other shapes, etc.

To further illustrate embodiment(s) of the present disclosure, various examples are given herein. It is to be understood that these examples are provided for illustrative purposes and are not to be construed as limiting the scope of the disclosed embodiment(s).

In the following examples, the present inventors have developed a unique technique(s) to incorporate agent(s) (e.g., protein) containing MNS/MNP into a nano-fibrous scaffold which is highly porous and interconnected. In one example, distinct multiple release of three model proteins from the scaffold has been achieved through the control over particle/sphere degradation rates. It is believed that the particle/sphere-scaffold system could serve as a multiple agent delivery carrier as well as a conductive matrix for tissue engineering applications.

EXAMPLE 1

Preparation of PLGA Microspheres

Poly(lactide-co-glycolide) (PLGA) microspheres were fabricated by a double emulsion technique. About 100 µl of an aqueous model protein solution (fluorescein isothiocyanate bovine serum albumin, FITC-BSA, tetramethylrhodamine isothiocyanate bovine serum albumin, TRITC-BSA, Alexa Fluor® 350 labeled bovine serum albumin, AF350-BSA, or TRITC-BSA/FITC-dextran) was emulsified into 1 ml of 10% PLGA/dichloromethane (DCM) solution, using a probe sonicator at 15 W (Virsonic 100, Cardiner, N.Y.) for 10 seconds over an ice bath to form the primary water-in-oil (w/o) emulsion. The w/o emulsion was mixed with 20 ml 1% PVA aqueous solution under sonication to form a water-in-oil-in-water (w/o/w) double emulsion. The solution was then stirred magnetically at room temperature for at least 3 hours to evaporate dichloromethane, and subsequently centrifuged to collect solid microspheres. The resultant microspheres were washed with distilled water twice, freeze dried and stored under vacuum.

Figure 1B:
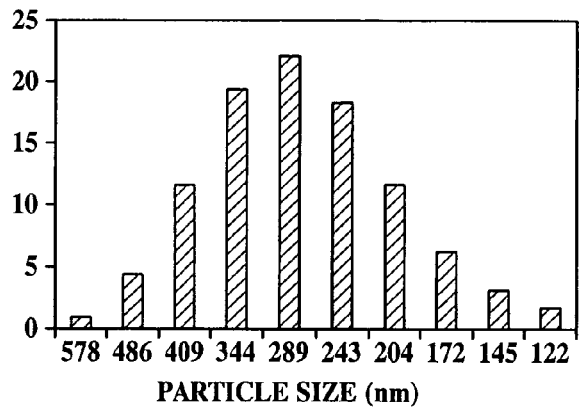
FIG. 1B is a graph depicting size distribution of PLGA50-64K microspheres, $D_{avg.}$=260 nm.

Three different PLGA copolymers were used for microsphere fabrication: PLGA50-6.5K, LA/GA=50/50, Mw=6.5 KDa; PLGA50-64K, LA/GA=50/50, Mw=64 kDa; PLGA75-113K, LA/GA=75/25, Mw=113 kDa. The microspheres have spherical shapes (FIG. 1A). The average size of the microspheres was 557 nm, 260 nm and 345 nm for PLGA50-6.5K, PLGA50-64K and PLGA75-113K, respectively, as determined by dynamic light scattering (L&N Microtrac Particle Analyzer 9200). The size of the microspheres was mainly controlled by the strength of sonication during emulsification. FIG. 1B shows the size distribution of PLGA50-64K microspheres. The loading efficiency was between about 75% and about 87% for BSA containing microspheres and about 47% for dextran containing microspheres, respectively.

EXAMPLE 2

Preparation of Macroporous Scaffold with Nano-Fibrous Structure

Three-dimensional macroporous nano-fibrous poly(L-lactide) (PLLA) scaffolds were prepared using sugar sphere template leaching and phase separation techniques as follows. First, sugar spheres with different sizes were prepared by an emulsion technique. Specifically, 50 grams of D-fructose (Sigma) was melted at 120° C. for 90 minutes until clear yellowish liquid was obtained. The liquefied sugar was emulsified into 50 ml mineral oil with 1.3 ml Span80 at 120° C. under stirring. The resulting mixture was cooled down using an ice-bath to solidify sugar spheres. After discarding the mineral oil, the sugar spheres were washed with hexane three times and sieved to select desired size (180-250, 250-425, 425-600 µm size ranges). The sieved sugar spheres were packaged in a Teflon vial with hexane and treated at 37° C. for a certain time to form a sugar template. After bonding the sugar spheres together, hexane was removed, and the sugar template was dried under vacuum.

About 0.6 ml to about 0.8 ml 10% PLLA/THF solution was cast into the assembled sugar template. Mild vacuum was applied during the casting in order to fully fill the interspaces of the bonded sugar sphere template with polymer solution. The polymer solution in sugar template was phase separated at a temperature ranging from about 20° C. to about −196° C. (in an embodiment, the temperature is equal to or less than 16° C.) overnight and then immersed into cyclohexane to exchange THF for 2 days. The resulting composites were freeze-dried, and the sugar was leached away in distilled water. The samples were freeze-dried again to obtain highly porous nano-fibrous scaffolds.

Figure 2A:
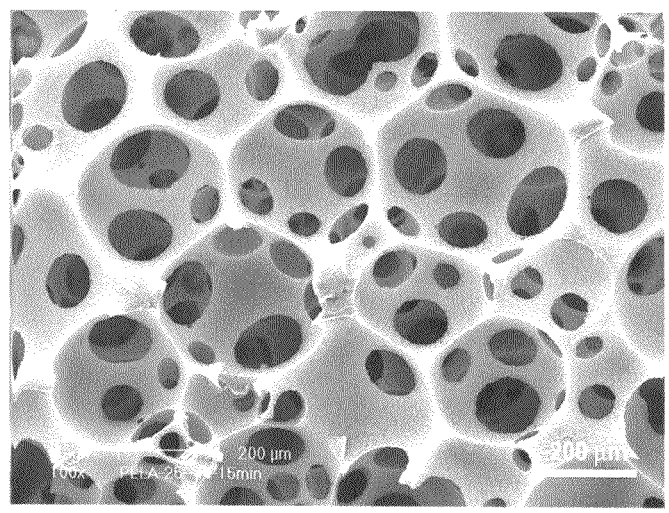
FIG. 2A is a SEM of a PLLA nano-fibrous scaffold at low magnification of 100×, showing well-interconnected macropores and inter-pore openings.
Figure 2B:
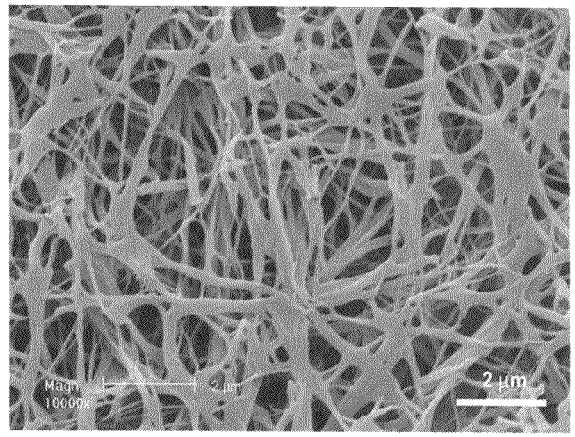
FIG. 2B is a SEM of a PLLA nano-fibrous scaffold at high magnification of 10,000×, showing nano-fibrous pore wall surfaces.

The scaffold has characteristics of high porosity (i.e., about 97.5%) well interconnected macroporous structures (e.g., macropores of about 250 µm-425 µm using about 250 µm-425 lm sugar spheres and inter-pore openings of about 80 µm-120 µm), and nano-fibrous pore wall structure (FIG. 2). It is believed that these features of the scaffold allow effective cell seeding and facilitate nutrient and waste transport during cell culture. It is to be understood that the porosity percentage and interconnect sizes of this example scaffold are meant to be illustrative and non-limiting. It is to be further understood that different porosity percentages and interconnect sizes may be more suitable for other applications (e.g., tissue engineering applications).

Furthermore, the phrase "high porosity" as used herein means porosity ranging from about 50% to about 99%.

EXAMPLE 3

Preparation of Macroporous Scaffold with Microporous or Solid Structure

Figure 3A:
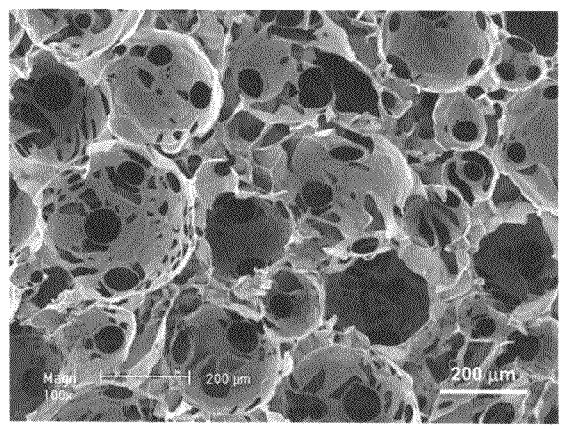
FIGS. 3A and 3B are each SEMs of PLLA microporous/solid scaffolds, showing a PLLA macroporous scaffold with microporous pore wall structures.
Figure 3B:
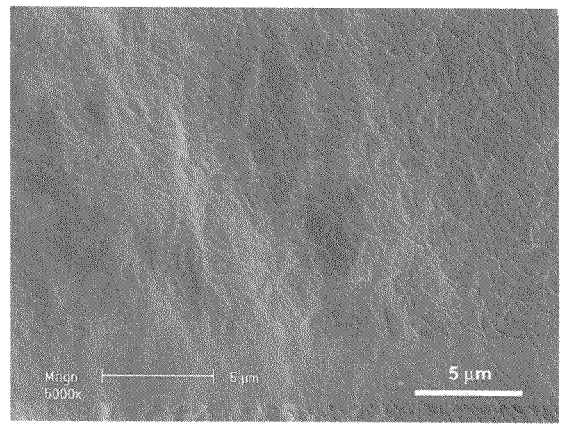

The procedures used for fabrication of nano-fibrous scaffolds were applied to prepare macroporous scaffold with microporous or "solid" pore walls by choosing different solvent systems. Instead of THF, dioxane and dichloromethane were used to create microporous structure (FIGS. 3A & 3B) and solid pore wall structure (FIGS. 3C & 3D), respectively. The method used for solid scaffold fabrication are not restricted to poly(L-lactic acid) (PLLA) scaffolds. Many biodegradable polymers including, but not limited to poly(lactic-co-glycolic acid) (PLGA), poly(D,L-lactic acid) (PDLLA), polycaprolactone (PCL), polycarbonates, blends of these polymers, and combinations thereof can be used to fabricate scaffolds. Various synthetic non-degradable polymers, or natural macromolecules (degradable or non-degradable) can also be fabricated into porous materials using this process.

EXAMPLE 4

Incorporation of PLGA Microspheres into PLLA Nano-Fibrous Scaffold (Post-Seeding)

In post-seeding method(s), drug-containing PLGA50-64K (LA/GA=50/50, Mw=64 kDa) microspheres (MS) were suspended in substantially pure hexane or an ethanol/water mixture solvent with a concentration of 5 mg MS/ml. About 80 μl of the suspension was seeded onto each PLLA nano-fibrous scaffold (7.2 mm in diameter by 2 mm in thickness, prepared in Example 3), and the scaffold was left in air for about 30 minutes to evaporate solvent. After that, another 80 μl of suspension was dropped onto the other side of the scaffold. The whole procedure was repeated twice, resulting in about 1.6 mg of microspheres in each scaffold. The scaffold can be subjected to a mixture solvent of hexane/THF (volume ratio of 90/10) to adhere the microspheres to nano fibers in the scaffold, and was vacuum-dried for 3 days to remove the solvent. It is to be understood that two or more types of microspheres can be post-seeded into the scaffold simultaneously.

The distribution of microspheres in scaffold was examined using SEM and laser scanning confocal microscopy (LSCM, Bio-Rad MRC-600, exciting wavelength 488 nm and 568 nm for FITC and TRITC labeled proteins, respectively). The incorporation of microspheres did not substantially interfere with the macro and microstructures of the nano-fibrous scaffolds (FIGS. 4A & 4B). The microspheres were distributed substantially uniformly on the entire pore wall surfaces throughout the nano-fibrous scaffold and adhered to the nano fibers (FIGS. 4A-4E). By adjusting the concentration of microsphere suspension and seeding times, one can easily control the amount of microspheres incorporated into the scaffold, which, in turn, can modulate the dose of protein released from the scaffold. FIGS. 4B and 4C show the scanning electron micrographs of nano-fibrous scaffold in which about 1.6 mg and 0.16 mg microspheres were incorporated, respectively, into the scaffold. In FIG. 4C, the concentration of microsphere suspension used was 2 mg MS/ml, and one single seeding (80 μl suspension) was employed, as compared to 5 mg MS/ml and four seedings for FIG. 4B.

EXAMPLE 5

Figure 5A:
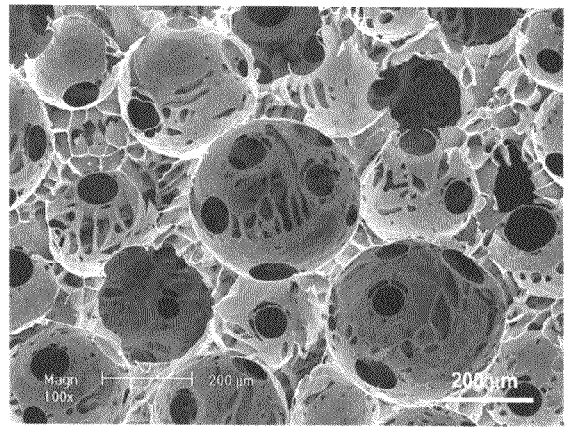
FIGS. 5A and 5B are each SEMs of PLLA microporous/solid scaffolds post-seeded with PLGA microspheres.
Figure 5B:
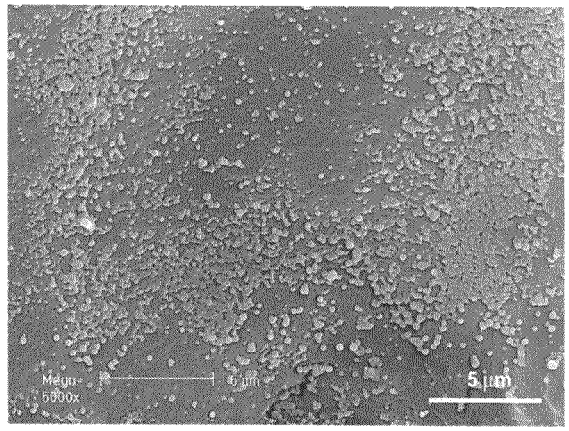
Figure 5C:
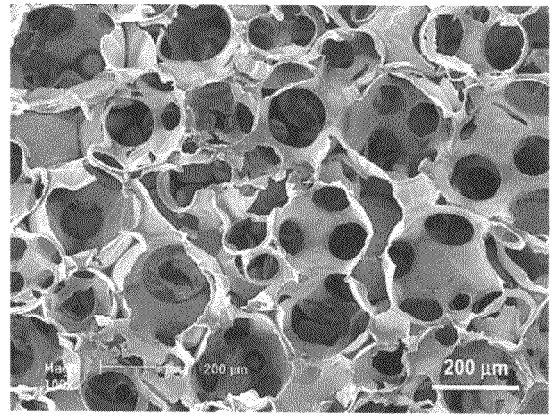

Incorporation of PLGA Microspheres into PLLA and PLGA85 Macroporous Solid Scaffolds—Post-Seeding PLGA50-6.5K microspheres (LA/GA=50/50, Mw=6.5 kDa) were also post-seeded into PLLA or PLGA85 (LA/GA=85:15) macroporous scaffolds with microporous or solid structures (developed in Example 4). Scanning electron micrographs demonstrated the well-interconnected macroporous structures with PLGA50-6.5K microspheres entrapped in entire internal pore wall surfaces throughout the scaffold (FIG. 5).

EXAMPLE 6

Incorporation of PLGA Microspheres into PLLA Solid Scaffolds Prepared by Traditional Solvent Casting/Salt-Leaching Method—Post-Seeding PLGA50-6.5K microspheres (LA/GA=50/50, Mw=6.5 kDa) were post-seeded into PLLA solid scaffolds prepared by traditional solvent casting/salt-leaching method. This is an example of an embodiment in which a previously fabricated porous material is used. The scaffold has irregular closed pore structures. The distribution of microspheres in the scaffold was not as uniform as those in the macroporous interconnected scaffold formed using an embodiment of the method disclosed herein (Example 4).

EXAMPLE 7

Effects of Solvent/Non-Solvent Post-Treatment on the Microsphere Morphology within the Scaffold In post-seeding methods for incorporation of microspheres into the scaffold, the post-treatment after seeding is generally an important factor for physically adhering microspheres to scaffold structures. A polymer solvent/non-solvent mixture (hexane/THF, ethanol/acetone, isopropanol/acetone) was chosen to treat the post-seeded microsphere-scaffold composites. About 80 μl solvent/non-solvent mixture was added to each microsphere-scaffold, which was then vacuum-dried. FIG. 6 shows the morphology of microspheres in scaffold after different solvent treatments.

EXAMPLE 8

Incorporation of PLGA Microspheres into Naturally Derived Polymer Scaffolds—Post-Seeding The post-seeding method can also be applied to incorporate PLGA microspheres into naturally derived polymers, such as chitosan, gelatin, and/or alginate scaffolds. Chitosan (85% deacetylated, Sigma) was dissolved in about 2% acetic acid to obtain a substantially homogeneous solution with concentrations of about 2.5 w/v %. The solution was freeze-dried to obtain a porous chitosan scaffold, which was then cross-linked in a 5% aqueous sodium citrate solution for 5 minutes and freeze-dried again. About 80 μl PLGA50-6.5K microsphere suspension in ethanol/water (80/20, v/v) was seeded into the chitosan scaffold (7.2 mm in diameter and 2 mm in thickness). The resulting microsphere-scaffold was vacuum dried.

EXAMPLE 9

Incorporation of Hydrophobic Microspheres into Scaffold (Pre-Seeding)

Figure 7B:
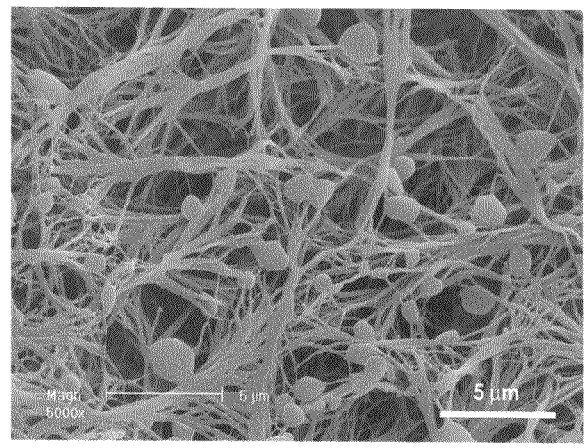
FIG. 7B is a SEM of a PLLA nano-fibrous scaffold pre-seeded with PLGA microspheres.

In an alternative pre-seeding method, PLGA microspheres were suspended in cyclohexane and seeded onto the sugar template. After evaporation of solvent, polymer casting and phase separation were performed following the same procedures used for scaffold fabrication (Example 3). The microspheres were entrapped in the nano-fibrous networks throughout the scaffold (FIG. 7). The maintained macroporous structure will advantageously allow the diffusion of proteins released from incorporated microspheres in the scaffold.

EXAMPLE 10

Preparation of Chitosan/Gelatin Microspheres

Hydrophilic chitosan/gelatin microspheres were prepared using an in situ emulsion cross-linking technique. Chitosan (85% deacetylated, Sigma) and gelatin (Type B from bovine skin, Sigma) were dissolved in 2% acetic acid at 37° C. to obtain a homogeneous solution with concentrations of 2.5 w/v % and 5 w/v % for chitosan and gelatin, respectively. FITC-BSA was added to the homogeneous solution in a concentration of 2.5 mg/ml. About 2 ml of FITC-BSA/chitosan/gelatin solution was dropped slowly under sonication (15W) to 50 ml of soybean oil with 2 ml Span80 (pre-heated at 47° C.). The resulting emulsion was mechanically stirred at 37° C. for about 20 minutes, and was then rapidly cooled down in an ice bath for another 20 minutes to solidify the chitosan/gelatin microspheres. After that, about 10 ml of sodium citrate (5% aqueous solution) was added to cross-link the chitosan for about 20 minutes. The cross-linked microspheres were separated from oil by centrifugation and washed with 5% sodium citrate once, distilled water twice, 2-propanol twice, and acetone twice, and finally were vacuum dried.

Figure 8B:
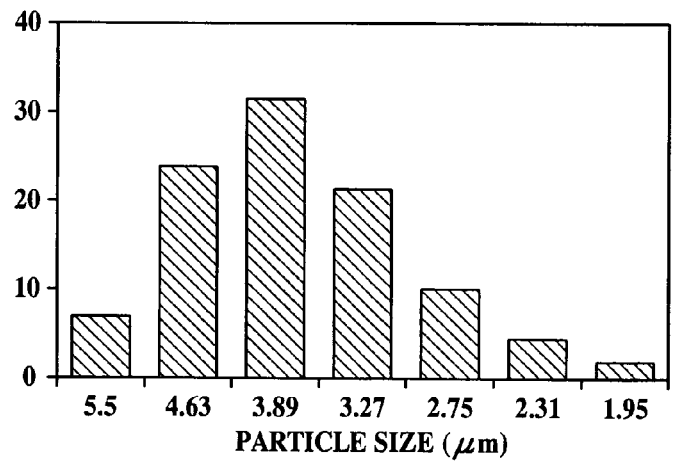
FIG. 8B is a graph depicting size distribution of the CG (chitosan/gelatin) microspheres, $D_{avg.}=3.51$ μm.
Figure 8A:
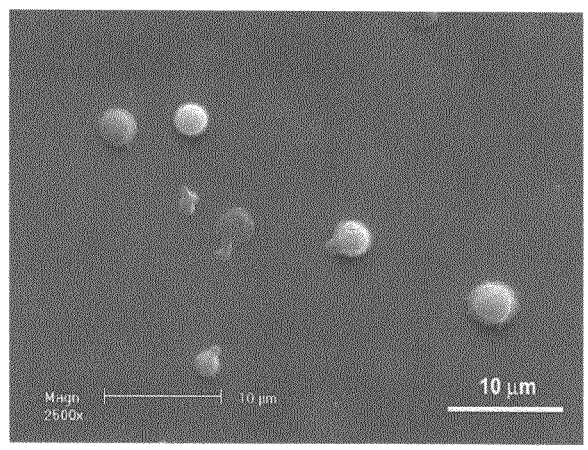
FIG. 8A is a SEM of chitosan/gelatin microspheres.
Figure 14C:
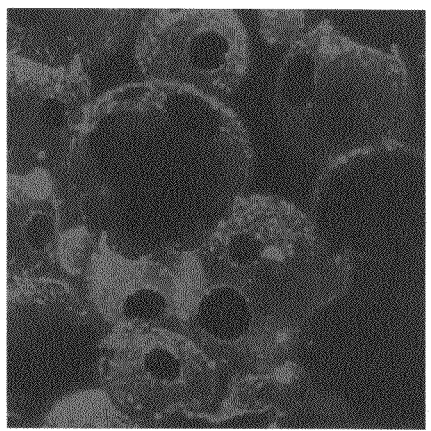
FIG. 14C is a Laser scanning confocal micrograph of a PLLA nano-fibrous scaffold post-seeded with TRITC-BSA/PLGA50-6.5K microspheres (red)
Figure 14D:
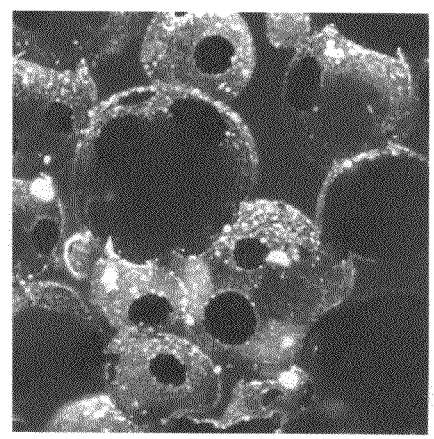
FIG. 14D is a Laser scanning confocal micrograph of a PLLA nano-fibrous scaffold post-seeded with a combination of the three types of microspheres from FIGS. 14A-14C.

The hydrophilic chitosan/gelatin (CG) microspheres were characterized using SEM and light scattering to have an average diameter of about 3.51 μm (FIGS. 8A and 8B). A loading efficiency of 63% was achieved. The degree of cross-linking may be controlled by varying the concentration of cross-linker (e.g. sodium citrate) and cross-linking time. Without being bound to any theory, it is believed that higher concentration and longer cross-linking time lead to higher degree of cross-linking, which thereby decreases the release rate.

EXAMPLE 11

Incorporation of Hydrophilic Microspheres into Macroporous Scaffold

Figure 9A:
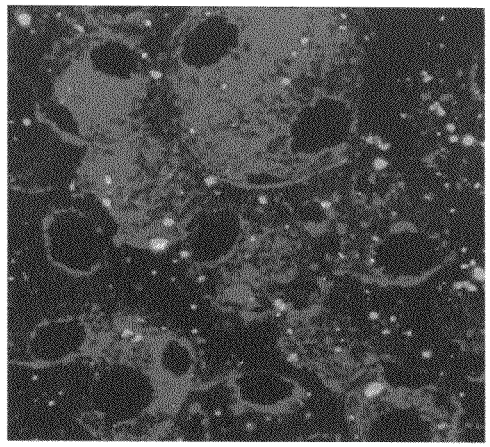
FIG. 9A is a Laser scanning confocal micrograph of a PLLA nano-fibrous scaffold pre-seeded with FITC-BSA-CG (chitosan/gelatin) (green) microspheres and post-seeded with TRITC-BSA/PLGA50-6.5K (red)
Figure 9B:
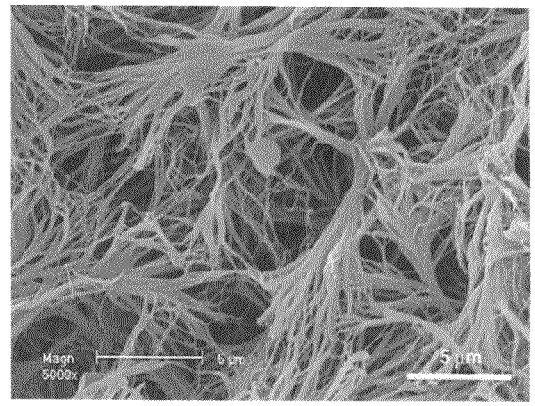
FIG. 9B is a SEM of CG microsphere pre-seeded PLLA nano-fibrous scaffold.

To incorporate hydrophilic chitosan/gelatin (CG) microspheres into nano-fibrous scaffold, CG microspheres were suspended in PLLA/THF solution and then cast into the sugar template followed by the same procedure for nano-fibrous scaffold fabrication (Example 3). Resulting scaffolds are shown in FIG. 9.

EXAMPLE 12

Figure 10A:
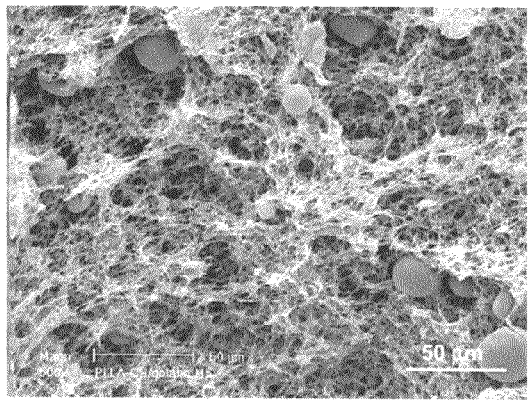
FIG. 10A is a SEM of chitosan/gelatin (CG) microsphere incorporated PLLA scaffold prepared by PLLA/THF phase separation at −20° C.
Figure 10B:
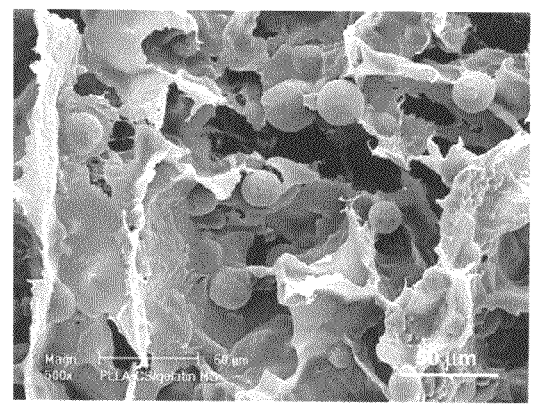
FIG. 10B is a SEM of chitosan/gelatin (CG) microsphere incorporated PLLA scaffold prepared by PLLA/dioxane phase separation at −20° C.

Incorporation of Hydrophilic Microspheres into Scaffolds Prepared by Phase Separation Hydrophilic chitosan/gelatin (CG) microspheres with diameters ranging from about 10 μm to about 30 μm were suspended in PLLA/THF or PLLA/dioxane solution homogenously under stirring. The mixture solution was then subject to phase separation at a temperature ranging from about 4° C. to about −196° C. overnight. The phase separated sample was then freeze dried to obtain final CG microsphere incorporated nano-fibrous (FIG. 10A) or solid scaffolds (FIG. 10B).

EXAMPLE 13

Degradation of PLGA Microspheres and Microsphere-Incorporated Scaffold

Figure 11:
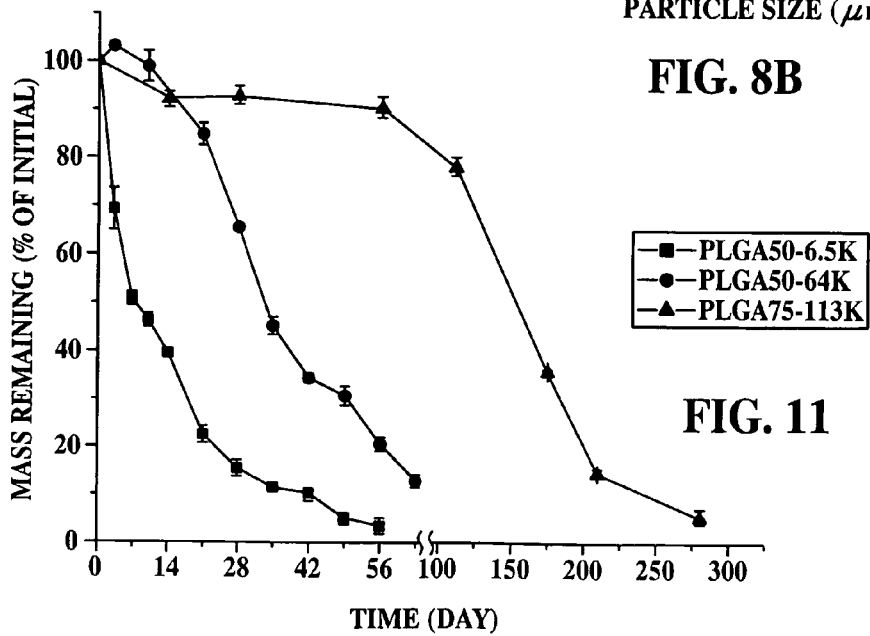
FIG. 11 is a graph depicting degradation studies of three PLGA microspheres, with the mass loss of different microspheres shown as a function of degradation time (Average±SD, n=3)

The degradation of microspheres was conducted in phosphate saline buffer (PBS, 10 mM, pH=7.4). About 10 mg of microspheres (three different microsphere formulations: PLGA50-6.5K, PLGA50-64K, and PLGA75-113 K) were suspended in 1 ml PBS and incubated at 37° C. under continuous orbital shaking at 60 rpm. At various time points, the microspheres were collected by centrifugation, washed with distilled water twice, and vacuum-dried. The mass loss was obtained as a function of degradation time. The degradation rate of three microspheres was dramatically different because of different molecular weights and LA/GA ratios of the copolymer (FIG. 11). PLGA50-6.5K microspheres degraded very fast with 80% of mass loss within 3 weeks while the mass of PLGA75-113K microspheres was not reduced significantly in 8 weeks. PLGA50-64K microspheres were quickly degraded after a 2-week degradation delay. The results indicate that the degradation rate of the microspheres may be modulated by varying the molecular weight and the ratio of lactide/glycolide of PLGA copolymer.

Figure 12C:
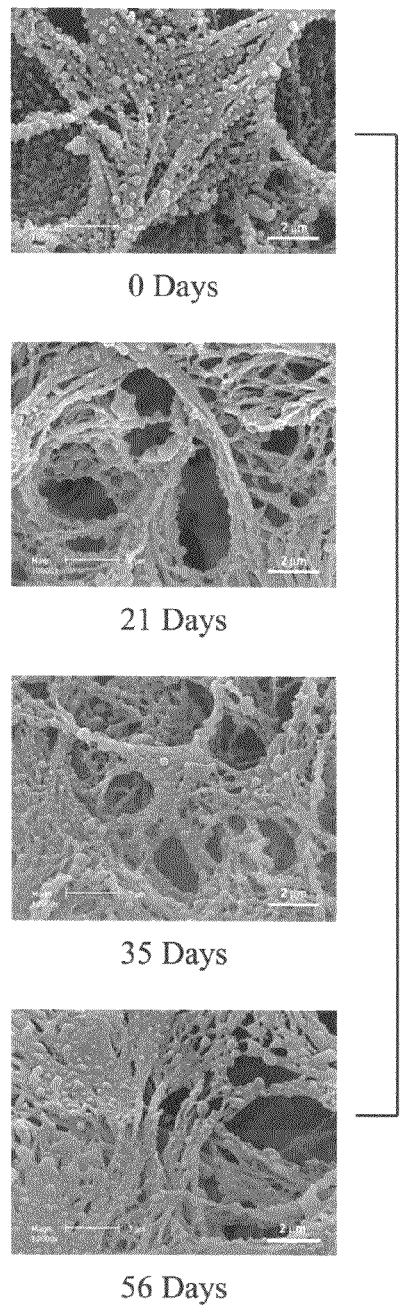
FIG. 12C is a degradation characterization of PLGA microspheres after post-seeded into PLLA nano-fibrous scaffold using scanning electron microscopy at 10,000×, PLGA75-113K at 0, 21, 35, 56 days.
Figure 14A:
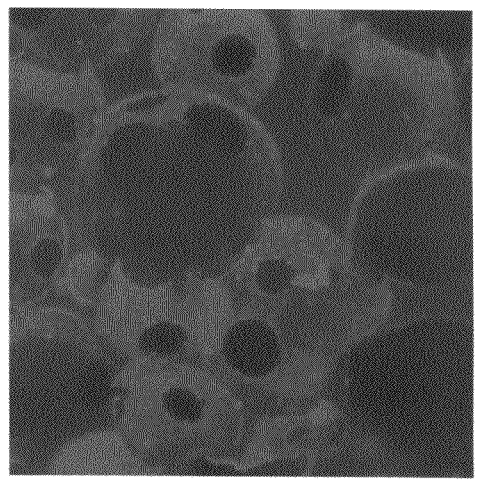
FIG. 14A is a Laser scanning confocal micrograph of a PLLA nano-fibrous scaffold post-seeded with AF350-BSA/PLGA75-113K microspheres (blue)
Figure 14B:
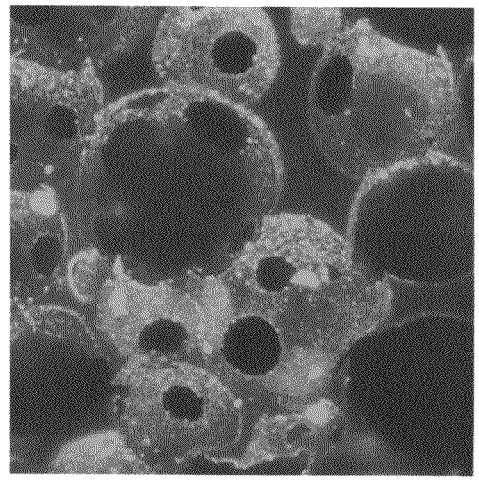
FIG. 14B is a Laser scanning confocal micrograph of a PLLA nano-fibrous scaffold post-seeded with FITC-BSA/PLGA50-64K microspheres (green)

The degradation of microspheres after incorporation into the scaffold (post-seeding) was also monitored by SEM for morphology changes (FIG. 12). Spherical microspheres attached to the nanofibers were initially separate. During degradation, the microspheres changed to a deformed irregular morphology, then merged together with nano fibers, and finally disappeared to expose the original nano fibers. The total degradation times of PLGA50-6.5K and PLGA50-64K are 3 weeks and 5 weeks, respectively. However, most PLGA75-113K microspheres remained unchanged in the scaffold after 8 weeks.

EXAMPLE 14

Protein Release Kinetics from Microspheres

Figure 13:
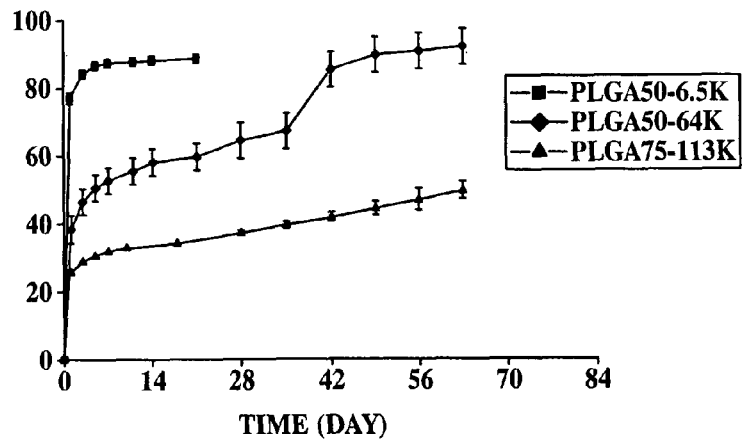
FIG. 13 is a graph depicting release of FITC-BSA from PLGA microspheres in PBS.

In vitro release of microspheres alone was carried out in PBS according to the same procedure for degradation. The release profiles of a model protein (BSA) from three microsphere formulations (PLGA50-6.5K, PLGA50-64K, PLGA75-113K) followed the degradation kinetics of the polymers, except for the initial burst release and a slight delay for subsequent sustained release (FIG. 13). BSA was released from the PLGA50-6.5K microspheres very fast, more than 90% of BSA was released within 7 days. PLGA50-64K microspheres exhibited a multi-phasic release pattern, starting from initial burst release of 40% in 1 day, followed by a slow and sustained release of 20% between day 3 and day 35, then a second burst release of 20% between day 35 to day 42 followed by another sustained release of the remaining BSA. It is believed that the second burst release resulted from degradation of the polymer. PLGA75-113K microspheres exhibited a sustained slow release in 0.4% per day for 60 days after an initial burst release of 28%.

EXAMPLE 15

Design of Microsphere-Incorporated Nano-Fibrous Scaffold for Multiple Protein Release To design a multiple protein delivery system, a macroporous nano-fibrous scaffold has been chosen for the incorporation of three protein-loaded microspheres (TRITC/PLGA50-6.5K, FITC/PLGA50-64K and AF350/PLGA75-113K) (FIGS. 14A-14D). The three-dimensional interconnected porous structure of the scaffold was well maintained.

In vitro release study of microsphere incorporated scaffold (MS-scaffold) was carried out in 1 ml PBS with 5 mM SDS (sodium dodecyl sulfate) at 37° C. under orbital shaking. Samples of release medium were taken at various time points and analyzed on a fluorometer (Fluoromax-2) for fluorescent BSA detection. The exciting/emission wavelengths are 495/515 nm for FITC, 544/570 nm for TRITC, and 346/442 nm for AF350, respectively.

Figure 14E:
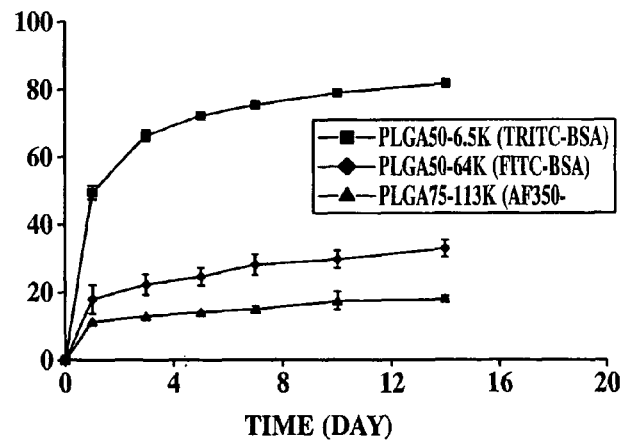
FIG. 14E is a graph depicting multiple protein release profiles from microsphere-incorporated nano-fibrous scaffold (TRITC/PLGA50-6.5K, FITC/PLGA50-64K and AF350/PLGA75-113K)

The multiple release of three labeled BSA from one single scaffold was shown in FIG. 14E. In a two-week time period, three distinct release profiles were obtained. The initial burst release of all three labeled proteins from scaffold was reduced as compared to that from microsphere alone. After initial release, the scaffold releases TRITC-BSA (from PLGA50-6.5K microspheres) at a fast rate of 3% per day while releases FITC-BSA and AF350-BSA at relative slower rate of 1% and 0.5% per day, respectively from PLGA50-64K and PLGA75-113K microspheres (incorporated in the scaffold). The results demonstrated that the developed MS-scaffold system was capable of releasing multiple factors with individualized release profiles.

EXAMPLE 16

Dual Protein Release Kinetics from Microspheres-Incorporated Scaffold

Figure 15A:
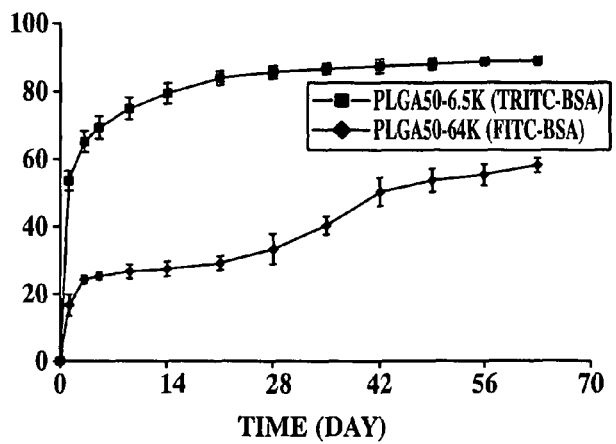
FIG. 15A is a graph depicting dual release profiles from microsphere-incorporated nano-fibrous scaffolds post-seeded with TRITC-BSA/PLGA50-6.5K and FITC-BSA/PLGA50-64K microspheres.
Figure 15B:
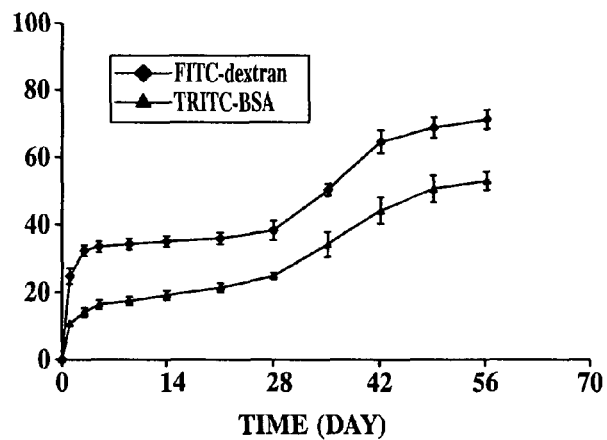
FIG. 15B is a graph depicting dual release profiles from microsphere-incorporated nano-fibrous scaffolds post-seeded with PLGA50-64K microspheres of TRITC-BSA and FITC-dextran.

To study the effect of microsphere composition and incorporation method on release kinetics in the long term, a variety of dual release patterns were achieved by incorporating two different microspheres, or by using different incorporation techniques (FIGS. 15A-15D). FIG. 15A shows individualized release profiles of the two proteins, i.e., TRITC-BSA (in PLGA50-6.5K MS) and FITC-BSA (in PLGA50-64K MS) from a PLLA scaffold. The release pattern from the MS-scaffold consists of a fast release of TRITC-BSA and a multiphasic release of FITC-BSA, which was similar to that from the two microspheres alone. However, the initial burst release was significantly reduced for both proteins when the microspheres were incorporated into the scaffold. The sustained release of TRITC-BSA (from PLGA50-6.5K) was extended to 28 days while 40% of FITC-BSA (from PLGA50-64K) was retained in the scaffold, even after 9 weeks. When two different macromolecules (TRITC-BSA and FITC-dextran) were encapsulated into the same PLGA50-64K microspheres (which were subsequently post-seeded on the scaffold), another type of dual release was obtained. TRITC-BSA and FITC-dextran were released in a similar pattern but in different dosage amounts (FIG. 15B). In contrast to TRITC-BSA, FITC-dextran was released faster because of its higher water solubility and smaller molecular chain size.

EXAMPLE 17

Figure 15C:
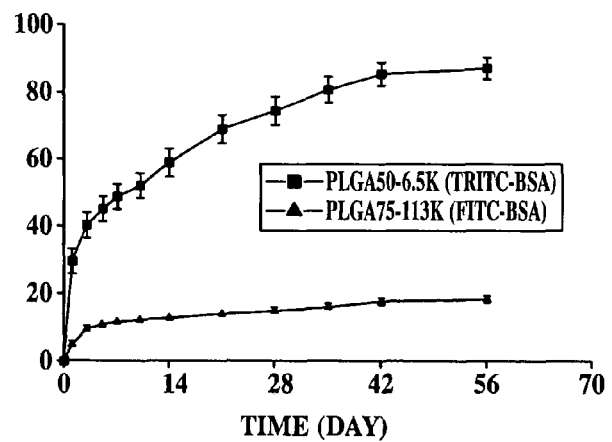
FIG. 15C is a graph depicting dual release profiles from microsphere-incorporated nano-fibrous scaffolds pre-seeded with TRITC-BSA/PLGA50-6.5K and FITC-BSA/PLGA75-113K microspheres.

Drug-Containing Microspheres were Also Incorporated into the Scaffold by a Pre-Seeding Method PLGA50-6.5K (TRITC-BSA) and PLGA75-113K (FITC-BSA) microspheres were incorporated into the PLLA nano-fibrous scaffold by methods previously described herein. The dual release profile from the scaffold consisted of a fast sustained release (1.2% per day for 40 days) for TRITC-BSA and a slow sustained release (0.16% per day for 50 days) for FITC-BSA (FIG. 15C).

EXAMPLE 18

Figure 15D:
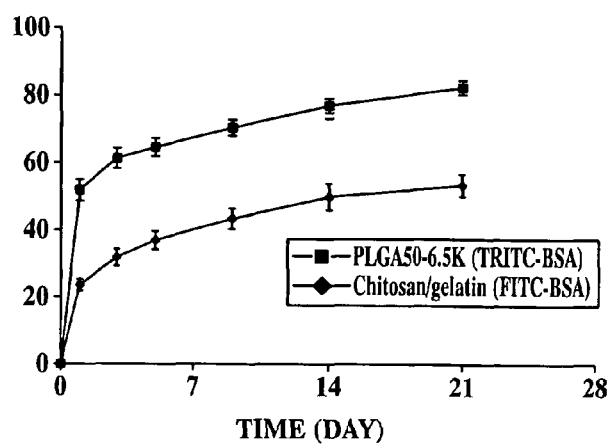
FIG. 15D is a graph depicting dual release profiles from microsphere-incorporated nano-fibrous scaffolds pre-seeded with FITC-BSA/CG and post-seeded with TRITC-BSA/PLGA50-6.5K microspheres.

PLGA50-6.5K (TRITC-BSA) Microspheres and Hydrophilic Chitosan/Gelatin (FITC-BSA) Microspheres were Incorporated into the Scaffold to Achieve a Dual Fast Release Profile Because of the fast degradation rate of PLGA-6.5K microspheres and the physical ionic cross-linking characteristic of CG microspheres, both proteins were released fast from the MS-scaffold (FIG. 15D).

These particle-containing porous materials can be used for various tissue regeneration/engineering applications. These applications include in vitro methods, in vivo implantation, or their combination. For in vitro tissue regeneration/engineering, cells are essential. The cells can be stem cells, such as embryonic stem cells or adult (tissue derived) stem cells, e.g., marrow derived stem cells (MSC). The cells may also be differentiated cells (chondrocytes, osteoblast, hepatocyte, fibroblasts, muscle cells, cardiac cells, endothelial cells, epithelial cells, adipose cells, neurons, pancreatic islet cells, or the like, or combinations thereof). For in vivo applications, cells are optional. In certain situations, such as a small or a thin layer of defect, cells may be recruited from the host tissues by the particle-containing porous materials. For some other situations, such as large defects or the lack of the needed cells at the implant site, cells may be incorporated in these porous materials to regenerate/repair tissues.

For example, to regenerate liver, hepatocytes and sinusoidal endothelial cells can be co-cultured on such a particle-containing porous material. The cells may alternatively be stem cells or partially from stem cells. The constructs can be cultured in vitro or implanted in vivo. In the particles, various factors such as HGF, VEGF, bFGF, PDGF, or the like, may be incorporated to release over time, thereby enhancing hepatic tissue growth and vascularization.

In another example, to regenerate bone, cells (osteoblasts, MSC, and/or ES cells) may be incorporated into the particle-containing porous materials. BMPs (such as BMP-2,4,6,7), Dex, ascorbic acid, bFGF, VEGF, and/or PDGF may be incorporated into the particles with individually designed release profiles. These factors will be released in a manner to synergistically stimulate vascularized bone formation.

Still another example includes the regeneration of cartilage. Chondrocytes, MSC and/or ES cells are seeded into the particle-containing porous materials. TGF-β and/or other agents may be released from the particles to enhance cartilage formation.

Periodontal tissues may also be repaired using the particle-containing porous materials. BMPs, PDGF, bFGF, and/or VEGF may be released from the particles to achieved cell recruiting from the host, proliferation in the scaffolds, differentiation into cells to regenerate cementum, periodontal ligament, bone and the vasculature all together.

Blood vessels, heart valves, skin, tendons, ligaments, muscles, nerves, tooth tissues, and so forth can also be regenerated with the right cells and biological agents/factors in such complex scaffolds with controlled release capacity.

These particle-containing complex porous materials can be used for controlled release purposes, even if tissue regeneration is not the aim. The immobilized particles in an interconnected matrix allow more controlled release of the agents of interest because free-moving particles often form aggregates, which have different release profiles from that of an isolated particle.

Using microsphere pre- or post-seeding techniques, both hydrophobic PLGA microspheres and hydrophilic chitosan/gelatin microspheres were incorporated into biodegradable PLLA scaffolds. Notably, the macro-, micro- and nano-features after microsphere incorporation were well retained, and the microspheres were distributed substantially uniformly throughout the scaffolds. Without being bound to any theory, it is believed that the characteristics of the scaffold system will allow the factor/agent release from the microspheres (and/or nanospheres) and facilitate cell penetration and nutrient transport in subsequent tissue regeneration application.

Embodiments of the materials disclosed herein are advantageously capable of releasing multiple factors from scaffolds. Furthermore, the release kinetics may be regulated by the microspheres. Another advantageous feature of the materials is that the scaffold structure reduces the burst effects of the release. It is believed that this feature allows the modulation of multiple release profiles by selecting the materials for microsphere fabrication. For example, the release kinetics of PLGA microspheres may be tailored by the molecular weight and LA/GA ratio while that of chitosan/gelatin may be modulated by cross-linking strength (concentration and time for cross-linking). Still further, the bioactivity of encapsulated molecules (i.e., agents) may be preserved in the microspheres until release. The methods and materials disclosed herein allow the delivery of multiple molecules with individualized release profiles to be readily expanded to the delivery of multiple biologically active factors/agents, including hormones, growth factors and DNA for tissue engineering applications.

In summary, it has been demonstrated that a novel micro- or nano-sphere/particle-incorporated nano-fibrous scaffold system is capable of delivering multiple molecules with controlled and individualized profiles. The release characteristics may be tailored by varying the properties of microspheres (polymer composition, molecular weight, loading etc.) and the incorporation method.

While several embodiments have been described in detail, it will be apparent to those skilled in the art that the disclosed embodiments may be modified. Therefore, the foregoing description is to be considered exemplary rather than limiting.

What is claimed is:

1. A material capable of controllably releasing a biologically active agent, comprising:
   a three-dimensional porous polymer material having nano-fibrous walls, and pores formed throughout the material such that the material includes internal pore surfaces and external pore surfaces; and
   at least one of micro-particles or nano-particles immobilized directly onto at least one of the internal pore surfaces or the external pore surfaces throughout the three-dimensional porous polymer material, the at least one of the micro-particles or nano-particles including poly(lactic-co-glycolic acid) or poly(L-lactic acid) having the biologically active agent embedded therein.

2. The material as defined in claim 1 wherein the porous material has a porosity of at least 30%.

3. The material as defined in claim 1 wherein the biologically active agent is selected from proteins, hormones, DNA, RNA, nutrients, drugs, and combinations thereof.

4. The material as defined in claim 1 wherein the micro-particles have a size ranging from 1.95 μm to 5.5 μm and the nano-particles have a size ranging from 122 nm to 578 nm.

* * * * *